(12) United States Patent
Razvi et al.

(10) Patent No.: US 8,043,303 B2
(45) Date of Patent: Oct. 25, 2011

(54) HANDLE FOR INTERCHANGEABLE MEDICAL DEVICE

(75) Inventors: Hassan Razvi, London (CA); John Denstedt, Komoka (CA); Gary L. Butler, Bloomington, IN (US); Thomas L. Foster, Poland, IN (US); Frank J. Fischer, Jr., Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 356 days.

(21) Appl. No.: 12/177,446

(22) Filed: Jul. 22, 2008

(65) Prior Publication Data

US 2009/0030427 A1 Jan. 29, 2009

Related U.S. Application Data

(63) Continuation-in-part of application No. 10/679,007, filed on Oct. 3, 2003, now abandoned.

(60) Provisional application No. 60/416,035, filed on Oct. 4, 2002.

(51) Int. Cl.
*A61B 17/221* (2006.01)

(52) U.S. Cl. ........................ 606/113; 606/127

(58) Field of Classification Search ................. 606/110, 606/113, 114, 127, 1; 604/165.02, 165.03
See application file for complete search history.

(56) References Cited

U.S. PATENT DOCUMENTS

| | | | |
|---|---|---|---|
| 2,137,710 A | 12/1937 | Anderson | |
| 4,393,872 A | 7/1983 | Reznik et al. | 604/264 |
| 4,763,668 A | 8/1988 | Macek et al. | 600/564 |
| 4,872,456 A | 10/1989 | Hasson | |
| 4,968,678 A | 11/1990 | Ornstein | 514/326 |
| 5,057,114 A | 10/1991 | Wittich et al. | 606/127 |
| 5,064,428 A | 11/1991 | Cope et al. | 606/127 |
| 5,197,968 A | 3/1993 | Clement | 606/115 |
| 5,222,973 A | 6/1993 | Sharpe et al. | 606/206 |
| 5,254,088 A | 10/1993 | Lundquist et al. | 604/95.04 |
| 5,290,294 A | 3/1994 | Cox et al. | 606/108 |

(Continued)

FOREIGN PATENT DOCUMENTS

DE 24 28 319 A1 1/1976

(Continued)

OTHER PUBLICATIONS

Apr. 2, 2009 Non-Final Office Action, U.S. Appl. No. 11/591,376.

(Continued)

*Primary Examiner* — Ryan Severson

(74) *Attorney, Agent, or Firm* — Brinks Hofer Gilson & Lione

(57) ABSTRACT

A rigid extractor is revealed, a rigid device for use in percutaneous procedures to remove kidney stones directly from the kidneys. The rigid extractor uses a handle fixed to an outer rigid cannula, and an inner cannula to control an extraction device that may be removable from the inner cannula. The extractor is desirably used with a fluoroscope, in which the surgeon maneuvers the extractor with the aid of a view of the operating field provided by the fluoroscope. The surgeon then maneuvers the extractor to grasp the kidney stones and remove from the patient. The extractor may also be used with a nephroscope. The device may be used with a removable extraction device such as a basket, a grasper a pair of jaws, or a pair of scissors.

16 Claims, 13 Drawing Sheets

U.S. PATENT DOCUMENTS

| | | | | |
|---|---|---|---|---|
| 5,308,357 | A | | 5/1994 | Lichtman .............. 606/205 |
| 5,308,358 | A | | 5/1994 | Bond et al. |
| 5,318,040 | A | | 6/1994 | Kensey et al. |
| 5,318,589 | A | | 6/1994 | Lichtman .............. 606/205 |
| 5,330,482 | A | | 7/1994 | Gibbs et al. ............ 606/113 |
| 5,358,508 | A | * | 10/1994 | Cobb et al. ............. 606/174 |
| 5,376,094 | A | | 12/1994 | Kline ..................... 606/113 |
| 5,387,219 | A | | 2/1995 | Rappe .................... 606/108 |
| 5,496,330 | A | | 3/1996 | Bates et al. ............. 606/127 |
| 5,556,376 | A | * | 9/1996 | Yoon ....................... 604/15 |
| 5,643,282 | A | | 7/1997 | Kieturakis ............. 606/114 |
| 5,788,710 | A | | 8/1998 | Bates et al. ............. 606/127 |
| 5,906,622 | A | | 5/1999 | Lippitt et al. .......... 606/127 |
| 5,989,266 | A | * | 11/1999 | Foster .................... 606/127 |
| 6,071,281 | A | | 6/2000 | Burnside et al. ........ 606/41 |
| 6,099,534 | A | | 8/2000 | Bates et al. ............. 606/127 |
| 6,159,220 | A | | 12/2000 | Gobron et al. ......... 606/127 |
| 6,162,209 | A | | 12/2000 | Gobron et al. ......... 606/1 |
| 6,168,603 | B1 | | 1/2001 | Leslie et al. ............ 606/114 |
| 6,174,318 | B1 | | 1/2001 | Bates et al. ............. 606/127 |
| 6,183,482 | B1 | | 2/2001 | Bates et al. ............. 606/127 |
| 6,203,552 | B1 | | 3/2001 | Bagley et al. .......... 606/127 |
| 6,217,589 | B1 | | 4/2001 | McAlister .............. 606/128 |
| 6,224,612 | B1 | | 5/2001 | Bates et al. ............. 606/114 |
| 6,258,101 | B1 | | 7/2001 | Blake, III ............... 606/113 |
| 6,264,664 | B1 | | 7/2001 | Avellanet .............. 606/128 |
| 6,280,451 | B1 | | 8/2001 | Bates et al. ............. 606/127 |
| 6,302,895 | B1 | | 10/2001 | Gobron et al. ......... 606/127 |
| 6,342,062 | B1 | | 1/2002 | Suon et al. ............. 606/200 |
| 6,348,056 | B1 | | 2/2002 | Bates et al. ............. 606/114 |
| 6,350,266 | B1 | | 2/2002 | White et al. ........... 606/114 |
| 6,368,328 | B1 | | 4/2002 | Chu et al. ............... 606/114 |
| 6,368,338 | B1 | | 4/2002 | Konya et al. ........... 606/200 |
| 6,383,196 | B1 | | 5/2002 | Leslie et al. ............ 606/114 |
| 6,402,761 | B2 | | 6/2002 | McAlister .............. 606/128 |
| 6,464,710 | B1 | | 10/2002 | Foster .................... 606/158 |
| 6,491,698 | B1 | | 12/2002 | Bates et al. ............. 606/127 |
| 6,500,182 | B2 | | 12/2002 | Foster .................... 606/127 |
| 6,520,968 | B2 | | 2/2003 | Bates et al. ............. 606/113 |
| 6,527,781 | B2 | | 3/2003 | Bates et al. ............. 606/114 |
| 6,544,227 | B2 | | 4/2003 | Sahatjian et al. ....... 604/113 |
| 6,565,530 | B2 | | 5/2003 | Sahatjian et al. ....... 604/113 |
| 6,602,262 | B2 | | 8/2003 | Griego et al. .......... 606/113 |
| 6,626,915 | B2 | | 9/2003 | Leveillee ............... 606/114 |
| 6,652,537 | B2 | | 11/2003 | Mercereau et al. ..... 606/127 |
| 6,676,668 | B2 | | 1/2004 | Mercereau et al. ..... 606/127 |
| 6,692,484 | B1 | | 2/2004 | Karpiel et al. ......... 606/544 |
| 6,720,402 | B2 | | 4/2004 | Langer et al. .......... 528/76 |
| 6,730,097 | B2 | | 5/2004 | Dennis ................... 606/113 |
| 6,893,450 | B2 | | 5/2005 | Foster .................... 606/200 |
| 7,041,108 | B2 | | 5/2006 | Lippitt et al. .......... 606/127 |
| 7,241,299 | B2 | | 7/2007 | Gerard ................... 606/127 |
| 2003/0023258 | A1 | | 1/2003 | DuMontelle |
| 2003/0109874 | A1 | | 6/2003 | Dennis |
| 2003/0109889 | A1 | | 6/2003 | Mercereau et al. |
| 2004/0122445 | A1 | | 6/2004 | Butler et al. |
| 2004/0133213 | A1 | | 7/2004 | Bagley et al. |
| 2005/0192592 | A1 | | 9/2005 | Butler |

FOREIGN PATENT DOCUMENTS

| | | |
|---|---|---|
| DE | 2428329 A1 | 1/1976 |
| DE | 101 25 149 | 12/2002 |
| EP | 0446020 B1 | 1/1995 |
| EP | 0 512 729 B1 | 7/1995 |
| EP | 0538984 B1 | 3/1997 |
| EP | 0679071 B1 | 3/1999 |
| EP | 1348381 A2 | 10/2003 |
| WO | WO 95/09566 | 4/1995 |
| WO | WO 9604875 A1 | 2/1996 |
| WO | WO 9605773 A1 | 2/1996 |
| WO | WO 9717014 A1 | 5/1997 |
| WO | WO 9738632 A1 | 10/1997 |
| WO | WO 9742884 A2 | 11/1997 |
| WO | WO 0071036 A2 | 11/2000 |
| WO | WO 0180748 A2 | 11/2001 |
| WO | WO 03/009742 | 2/2003 |
| WO | WO 03/049625 A1 | 6/2003 |

OTHER PUBLICATIONS

Hoffman, Nathan et al., "Percutaneous Renal Stone Extraction: In Vitro Study of Retrieval Devices," The Journal of Urology, Copyright © 2004 by American Urological Association, vol. 172, Aug. 2004, pp. 559-561.

International Search Report from Canadian patent application No. 2,500,853 dated Nov. 14, 2008 (3 pages).

International Search Report from PCT application No. PCT/US2006/042637 dated Mar. 6, 2007 (6 pages).

International Search Report from PCT application No. PCT/US03/31688 dated Feb. 10, 2004 (8 pages).

Search Report dated Jul. 2, 2010 (published Aug. 18, 2010) for related EP 09 16 6143.

* cited by examiner

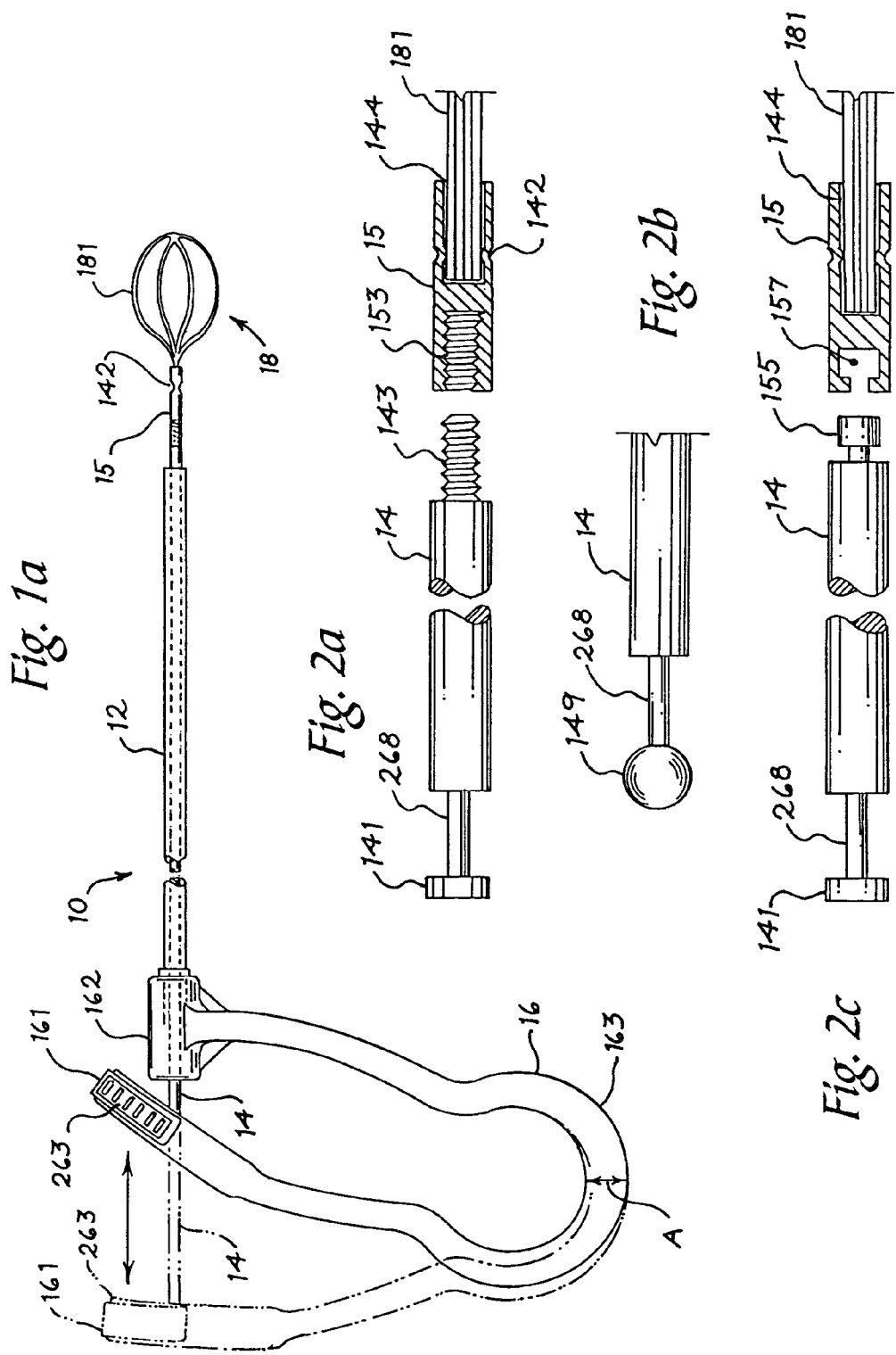

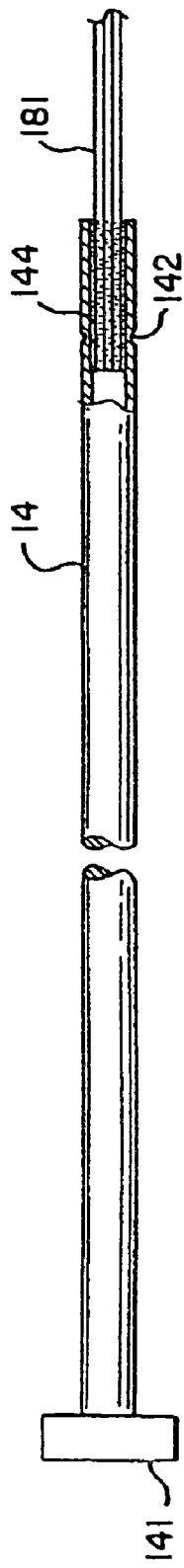
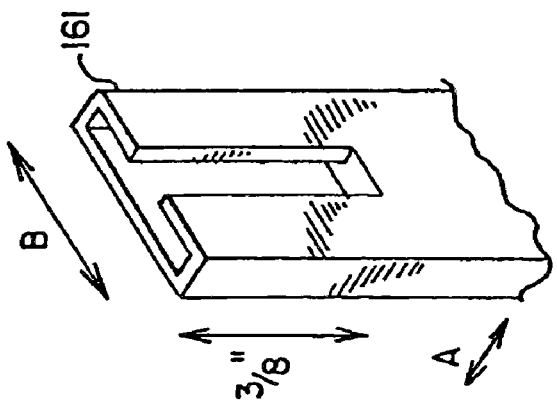
Fig. 2d
Fig. 3d

HANDLE FOR INTERCHANGEABLE MEDICAL DEVICE

This application is a continuation-in-part of U.S. patent application Ser. No. 10/679,007, filed Oct. 3, 2003, which claims the benefit of the filing date under 35 U.S.C. §119(e) of Provisional Application No. 60/416,035, filed Oct. 4, 2002, entitled Rigid Extractor, which is hereby fully incorporated by reference herein.

FIELD OF THE INVENTION

This invention relates generally to surgical retrieval devices. The device relates more particularly to devices for capturing and retrieving or extracting stones, calculi, concretions, foreign bodies and the like from a human or veterinary patient. The device may also be useful for biopsies and other surgical retrievals.

BACKGROUND OF THE INVENTION

Various organs and passages in the body are subject to the development of stones, calculi and the like. For example, kidney stones are a common problem in the United States. Kidney stones are painful and are the most frequent cause of kidney inflammation. Calculi and concretions in other parts of the biliary system are also commonplace. Similarly, stones, calculi, concretions and the like can develop throughout the renal or urinary system, not only in the ureters and distal to them, but also in the renal tubules and in the major and minor renal calyxes.

Minimally invasive surgical procedures have been developed for the removal of stones, calculi, concretions and the like from the biliary, vascular, and urinary systems, as well as for the removal or retrieval of foreign bodies from a variety of locations in the body. Such procedures avoid the performance of open surgical procedures such as, for example, an anatrophic nephrolithotomy. Minimally invasive procedures can instead employ percutaneous access, in which stones, calculi, concretions, foreign bodies and the like are removed through a percutaneously inserted access sheath. Several access routes are suitable, depending upon the specific system and the particular location in the system at which the stones, calculi, concretions, foreign bodies or the like are found. One access route that is infrequently used is direct percutaneous insertion of a retrieval device to remove calculi and kidney stones.

Without regard to the particular access route, percutaneous extraction may be based upon the use of catheters or similar devices to engage and remove the stones, calculi, concretions, foreign bodies and the like. Such catheters and devices typically comprise a hollow, flexible sheath and a plurality of wires positioned in and extendable from the sheath. The wires are joined or arranged so as to form a means, such as a basket or forceps for engaging the object to be retrieved when the wires are extended from the sheath. The wires may also form a continuum with the sheath. The engagement means (for example, a basket) can be collapsed by withdrawing the wires into the sheath. A helical basket permits entry of the stone or the like from the side of the basket, while an open ended ("eggwhip") basket allows a head-on approach to the stone or the like. Other retrievers and graspers can include forceps or can include a loop or snare for encircling the body to be removed, the loop or snare being made of the wire. Such devices may be used in conjunction with a nephroscope, to aid the physician in seeing the operating field. Using such a device also tends to limit the size of the cannula and basket used.

Despite their successful use for some time, such retrieval devices are subject to drawbacks. The principal device that is used to retrieve kidney stones is a 3-pronged grasper. The prongs of the grasper useful in grasping stones, may cause damage to kidney or contiguous tissue, leading to bleeding, and potentially significantly extending the time for the procedure. The very flexible, movable nature of these graspers adds to the problem, in that their flexibility and mobility make them more difficult to control.

It would be highly desirable to have a more controllable device for use inside the human body for the capture and retrieval or extraction of kidney stones and related calculi. The device preferably would not have sharp points that could scratch or puncture bodily tissue, and would be able to remove kidney stones up to one-quarter inch in diameter or even larger.

BRIEF SUMMARY

The foregoing problems are solved and a technical advance is achieved in an extractor for capturing, extracting, retrieving, or removing objects such as stones and calculi from the human body. Of course, the device is not limited to human bodies, but may also be used in veterinary applications. One embodiment is an extractor for removing an object from a location within a body. The extractor comprises an inner cannula, a handle for actuation, and a rigid outer cannula fixedly attached to the handle for delivering a removable extraction device to the location of the object to be removed. The removable extraction device can be removably secured to the distal end of the inner cannula. In this regard, a variety of different extraction devices may be used by removably securing an extraction device to the inner cannula, thus enabling the use of disposable extraction devices such as graspers or baskets.

There are many ways to practice the present invention, as shown in the following drawings and specification. The embodiments described below are not meant to limit the invention, but rather to describe and illustrate the many ways that the present invention may be used. The advantages of the invention include better control over the retrieval device used at the distal end of the cannula, as well as better retrieval devices themselves, leading to easier entry, less damage and bleeding, and shorter removal procedures.

BRIEF DESCRIPTION OF THE FIGURES

The present invention will now be described in conjunction with the following drawings, wherein like reference characters refer to like parts throughout the several views.

FIG. 1a is a plan view of a first embodiment of a rigid extractor.

FIG. 2a is a plan view of the proximal end of an inner cannula along with a sectional view of an extraction cannula according to one embodiment.

FIG. 2b is a plan view of an inner cannula according to the embodiment of FIG. 1.

FIG. 2c is a plan view of an inner cannula and extraction cannula according to one embodiment.

FIG. 2d is a plan view of an inner cannula and extraction cannula according to one embodiment.

FIG. 3a is a perspective view of a portion of the handle according to FIG. 1a.

FIG. 3b is a plan view of a handle cap according to FIG. 1a.

FIG. 3d is a perspective view of a portion of the handle according to FIG. 1b.

DETAILED DESCRIPTION OF THE PRESENTLY PREFERRED EMBODIMENTS

Figure 1B:
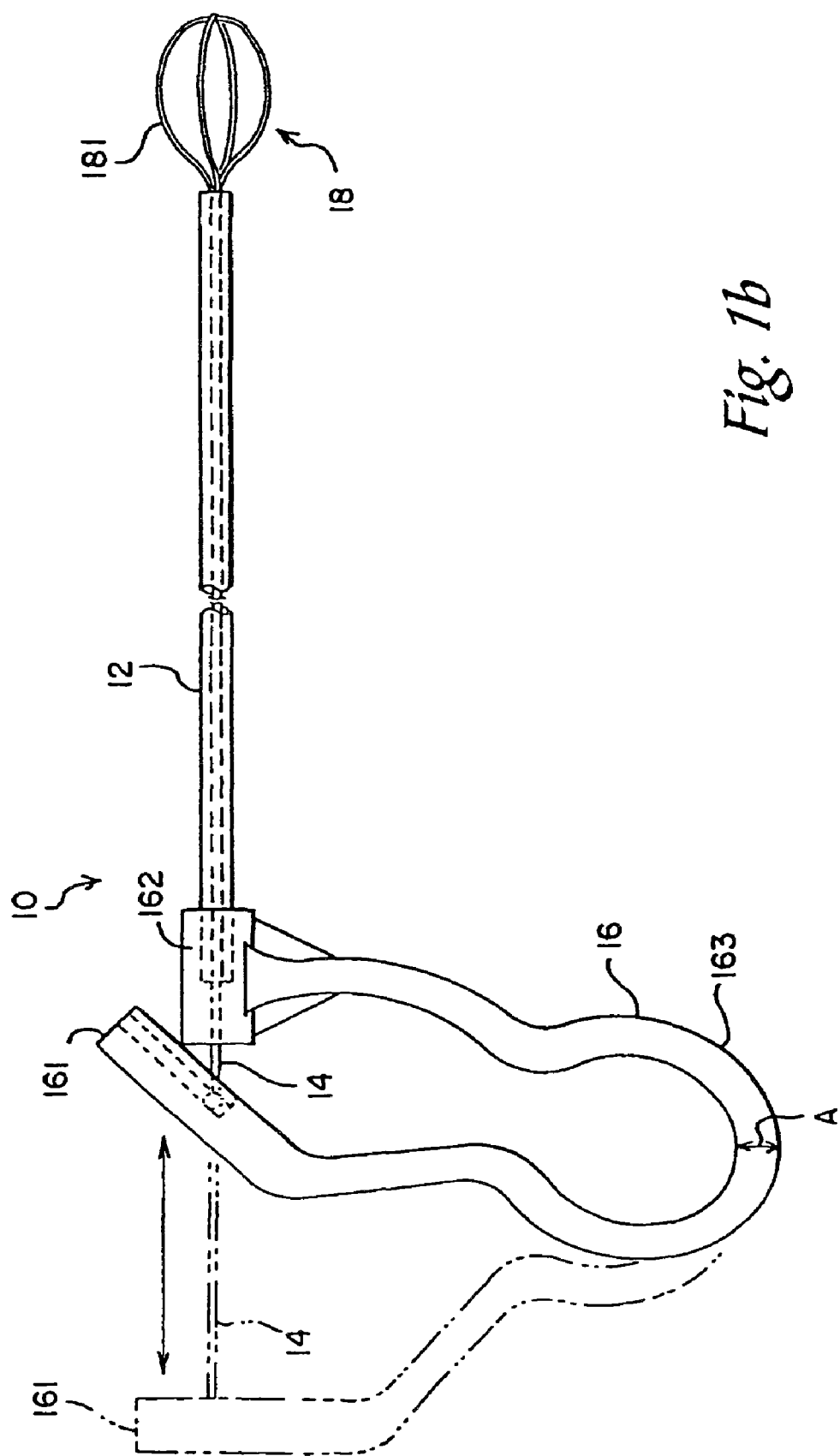
FIG. 1b is a plan view of another embodiment of a rigid extractor.

A first embodiment is a rigid extractor useful in grasping and removing kidney stones from a patient. The kidney stones will typically have been reduced in size by a procedure in which laser energy, electro-hydraulic energy, or sound energy is applied to reduce the stones in size for easier removal. A first embodiment is depicted in FIG. 1a. The rigid extractor 10 comprises a rigid outer cannula 12 and an inner cannula 14. The inner cannula 14 is secured to a removable extraction device 18, illustrated in FIG. 1a as a basket 18 formed from at least one wire loop 181. In another embodiment depicted in FIG. 1b, the extraction device 18 is not removable. The removable extraction device 18 of FIG. 1a is configured to be attached to an extraction cannula 15 of the same outer diameter as the inner cannula 14. The extraction cannula 15 is configured to be removably secured to the inner cannula 14. In the embodiment depicted in FIG. 2a, the inner cannula 14 and the extraction cannula 15 have mating threaded portions 143, 153 which can be screwed together, thus securing the extraction device 18 to the inner cannula 14. As discussed below, the removable extraction device 18 may be any of a number of different engagement means, such as forceps, graspers, loops, or various basket varieties available to surgeons. The extractor 10 also has a handle 16 for operating the extractor. The handle 16 comprises a first end 161 attached to the inner cannula 14, and a second end 162, attached to the outer cannula 12. The handle also comprises a gripping portion with a flexible section 163. In the embodiments shown in FIGS. 1a and 1b, the basket 18 is tipless, in the sense that there is no distal "end" to the basket in which the wires are secured to each other by soldering, welding, brazing, adhering, or the like.

The extractor 18 is operated by applying hand pressure to the handle 16, squeezing the handle 16, deflecting the first end 161 to the right in FIGS. 1a and 1b, and causing the inner cannula 14 to translate to the right, and extending the extraction device 18, here a basket. The handle 16 is shown in solid line in the "squeezed" position, and in dotted line in the "relaxed" condition. It is understood that the basket is extended from the outer cannula 12 as shown when the operator or surgeon applies pressure and squeezes the handle 16. When no pressure is applied to the handle 16, it is in a relaxed state, and the basket is collapsed within the outer cannula 12. The handle 16 is not meant for insertion into the body of a patient, but remains outside the body during procedures for removing objects from a body. The handle 16 preferably is made of nylon or other acceptable plastic. The handle 16 shown in FIGS. 1a and 1b has a length of about 3.5 inches (up and down) and the gripping portion has an inner diameter of about 1.05 inches and an outer diameter of about 1.50 inches. The thickness of the handle 16, in the direction of arrow A in FIGS. 1a and 1b, determines the force needed to deflect the handle 16 and extend the basket from the cannula. In a preferred embodiment, the thickness of the handle 16 is 0.225 inches, but it may also be from about 0.20 inches to about 0.25 inches, and may range from about 0.15 inches to about 0.30 inches. The width of the handle 16, perpendicular to the thickness direction shown, is preferably about 0.25 inches, but is not of particular importance, and may vary from about 0.125 inches to about 1 inch.

The thickness of the handle 16 is important because the thickness determines the force required to deflect the handle 16 and extend the basket. This force should be sufficient so that movement of the handle 16, and thus the basket, or other retrieval assembly on the distal end of the inner cannula, is deliberate but not difficult. In the course of conducting many tests, it was determined that a force of about five pounds is particularly preferred, while a force from about one pound to about eight pounds could be conveniently used. A force of about five pounds is necessary to deflect the handle 16 if it is made from nylon 6, in a thickness of about 0.225 inches. When the handle 16 is made with a thickness of about 0.150 inches, a force of about 1 pound is sufficient to operate the extractor. A thickness of over about 0.25 inches requires even greater force. The preferred thickness of the handle 16 is therefore from about 0.20 to about 0.25 inches, preferably about 0.225 inches, and nylon 6 is a preferred material.

The outer cannula 12 is a desirably rigid hollow tube that does not deflect appreciably in use. The extractor may be used with a nephroscope, in which the surgeon inserts the rigid extractor and its outer cannula 12 into an appropriate channel in the nephroscope. The nephroscope allows the surgeon to view the operating field as the surgeon maneuvers the nephroscope and the extractor to capture and remove objects within the body, such as kidney stones. The outer cannula 12 is sufficiently rigid for the surgeon to deflect and maneuver the nephroscope by using the outer cannula 12 of the rigid extractor. The outer cannula 12 is desirably made from a medically acceptable material such as stainless steel or stiff plastic material, preferably those with minimal coefficients of friction, such as reinforced plastic, stiff polyimide, PTFE, and other medically acceptable materials. 316 stainless steel is a preferred material. The outer cannula 12 may vary in length from about 20 cm to about 60 cm. An intermediate length of about 38 cm works well with most patients and is preferred.

The outer cannula 12 preferably has a wall thickness of at least 0.010 inches, desirably 0.014 inches, and more preferably 0.015 inches. The greater the wall thickness, the more rigid will be the outer cannula 12. This rigidity enables the surgeon to control the nephroscope and to maneuver the nephroscope into a desired position. The surgeon thus delivers the outer cannula 12 and the basket 18 to the desired location within the operating field. The outer cannula 12 may preferably have an outer diameter from about 0.110 inches to about 0.200 inches, or from about 8.5 Fr to about 15.5 Fr. The inner diameter of the outer cannula 12 depends on the dimension of the outer cannula 12 and sufficient wall thickness to maintain the desired rigidity. Therefore, the inner diameter of the outer cannula 12 may preferably range from about 0.080 inches to about 0.175 inches (from about 6 Fr. to about 13.5 Fr.). It is understood that wall thicknesses are preferably maintained at a minimum of 0.015 inches, but wall thicknesses slightly less than 0.015 inches may also be used.

Figure 4A:
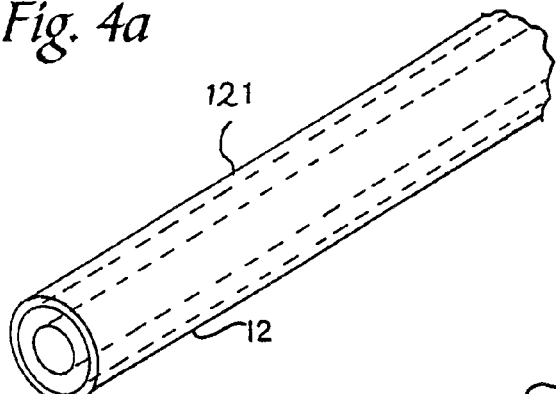
FIGS. 4a and 4b are perspective and cross-sectional views of the rigid outer cannula according to FIGS. 1a and 1b.
Figure 4B:
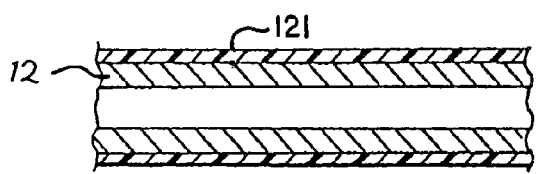

The outer cannula 12 may be covered with a thin adherent plastic covering, in order to aid the physician in placing the extractor. The covering is desirably a medical grade plastic material, such as Teflon® (PTFE) or other grade of plastic or fluoropolymer. These may include FEP, fluorinated ethylene propylene, PFA, perfluoroalkoxy polymer, and other medically-acceptable grades of thermoplastic or thermoset coatings. The covering is desirably thin, preferably about 0.10 to about 0.4 mm thick (about 0.004 to about 0.015 inches thick). FIGS. 4a and 4b depict an outer cannula 12 and a thin plastic covering 121 on the outer diameter of the cannula.

The inner cannula 14 is preferably a solid rod, also made from stainless steel, although a hollow rod or tubing may also be used. The outer diameter of the inner cannula must fit within the inner diameter of the outer cannula 12, with sufficient clearance for easy movement within the outer cannula 12. The inner cannula is desirably at least about 0.065 inches in diameter (about 5 Fr). Other diameters may be used.

In the embodiment depicted in FIG. 2a, the inner cannula 14 and the extraction cannula 15 have mating threaded portions 143, 153 which can be screwed together, thus securing the extraction device 18 to the inner cannula 14. Alternatively, the extraction cannula 15 and the inner cannula 14 may be removable secured together with a snap fit connection as shown in FIG. 2c, or any other means known in the art. The snap fit connection is made with a male portion 155 on the inner cannula 14, and a female portion 157 on the extraction cannula 15. Alternatively, the male and female portions of the threaded or snap fit connections may be reversed.

The extraction cannula 15 preferably has substantially the same outer diameter as the inner cannula 14. The extraction cannula 15 may also have a short portion on its distal end hollowed out so that the wire loops and legs used to make the basket may fit into the distal end of the extraction cannula 15. The wires are then desirably crimped to the extraction cannula 15, as shown in FIG. 2a at location 142. They may also be secured to the inner cannula with an adhesive 144, such as a medically-acceptable grade of cyanoacrylate adhesive. Loctite 4011 works well and is preferred. As discussed below, the removable extraction device 18 may be any of a number of different engagement means, such as forceps, graspers, loops, or various basket varieties available to surgeons.

Of course, other embodiments of the rigid extractor may be smaller. One embodiment of a rigid extractor outer cannula 12 has an outer diameter of about 4.5 Fr, about 0.059 inches, and an inner diameter of about 0.0465 inches with a nominal wall thickness of about 0.0065 inches. In this embodiment, the inner cannula 14 and extraction cannula 15 have an outer diameter of about 0.0425 inches and an inner diameter of about 0.0315 inches. In order to make the cannula slightly stiffer on the proximal end, a plug about 3 or 4 inches long was adhered to the proximal end of the inner cannula, near the point where it attaches to the handle 16. The particular embodiment was made of 316 stainless steel. Other materials suitable for the application may also be used. While this cannula is less rigid than one with walls 0.010 inches thick, it is much easier to control than a "flexible" cannula.

Figure 3A:
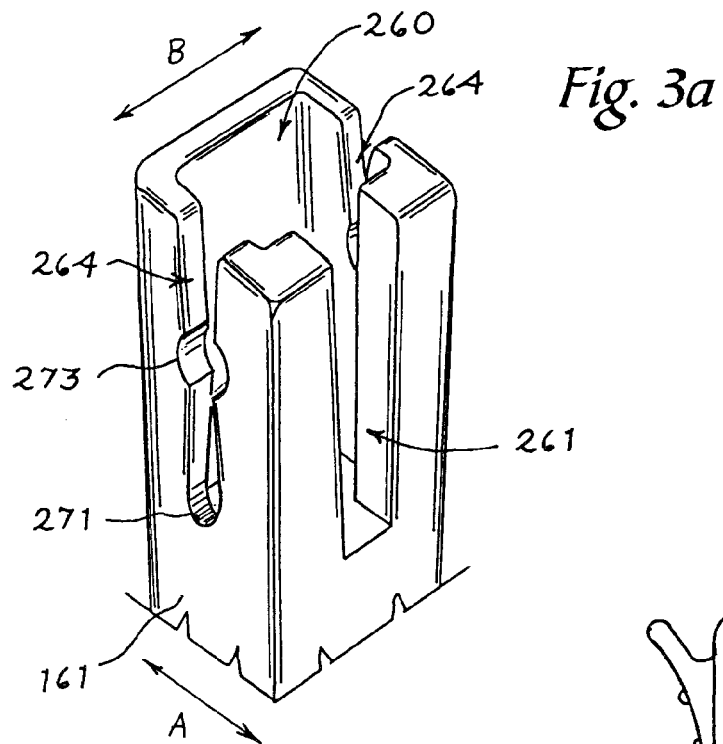

FIG. 2a depicts an inner cannula 14 with a restriction member in the form of a T-shaped fitting 141 on the proximal end of the inner cannula, for fitting into a matching slot 261 in the first end 161 of the handle 16. The slot 261 is illustrated in FIG. 3a. FIG. 2a also depicts a cross section of an extraction cannula 15, which has at least one wire 181 secured to the cannula by a crimp 142 at the distal end of the cannula. The wires may also be secured with adhesive 144 as shown.

FIG. 2b depicts an alternative embodiment of the proximal end of the inner cannula wherein the T-shaped fitting restriction member is replaced by a cylindrical T-bar 149. One of skill in the art will appreciate that other geometries may also be used as a restriction member to confine the proximal end of the inner cannula within the cavity 260 formed in the first end 161 of the handle 16, such as a spherical bulb or a rectangular prism. Regardless of the embodiment, the restriction member is preferably attached to the proximal portion of the inner cannula 14 with a narrow rod 268 of a diameter preferably about half the diameter of the inner cannula 14. The proximal end of the inner cannula is designed to remain within the slot 261 so that when the handle 16 is actuated, the inner cannula may be pushed to extend the extraction device.

FIG. 2d depicts an inner cannula 14 with a T-shaped fitting 141 on the proximal end of the inner cannula, for fitting into a matching slot in the first end 161 of the handle 16. The inner cannula 14 also has at least one wire 181 secured to the cannula by a crimp 142 at the distal end of the cannula. The wires may also be secured with adhesive 144 as shown. FIG. 3d depicts a close view of the first end 161 of the handle used to operate the rigid extractor of FIG. 1b. The first end 161 includes a hollow portion forming a slot as shown, to receive the T-shaped fitting 141 of the proximal end of the inner cannula. The first end may have a thickness designated in the direction of arrow A, and may have a width as shown in the direction of arrow B. The slot may extend a short distance into the first end of the handle, the distance being sufficient so that the inner cannula is not easily dislodged from the first end. A distance from about 0.25 inches to about 0.50 inches (about 6 to about 13 mm) is sufficient; about 0.375 inches (9-10 mm) is preferred.

FIG. 3a depicts a perspective view of the first end 161 of the handle 16 used to operate the rigid extractor. The first end 161 includes a hollow portion forming a slot 261 as shown, which opens towards the distal end to receive the restriction member, preferably the T-shaped fitting 141, of the proximal end of the inner cannula. The first end 161 may have a thickness designated in the direction of arrow A, and may have a width as shown in the direction of arrow B. The slot may extend a short distance into the first end of the handle 16, the distance being sufficient so that the inner cannula is not easily dislodged from the first end. A distance from about 0.25 inches to about 0.50 inches (about 6 to about 13 mm) is sufficient; about 0.375 inches (9-10 mm) is preferred.

The T-shaped fitting 141 or alternative restriction member should be sized such that it can fit through and be pulled out of the slot 261. Preferably the T-shaped fitting has the same height and width, or diameter, as the diameter of the inner cannula. This enables the user to easily pull the inner cannula 14 distally through the outer cannula 12 if need be should complications arise during a procedure. In the ordinary course of operation, however, a cap 263 is provided to secure the proximal end of the inner cannula within the cavity 260 of the first end of the handle 16.

Figure 3B:
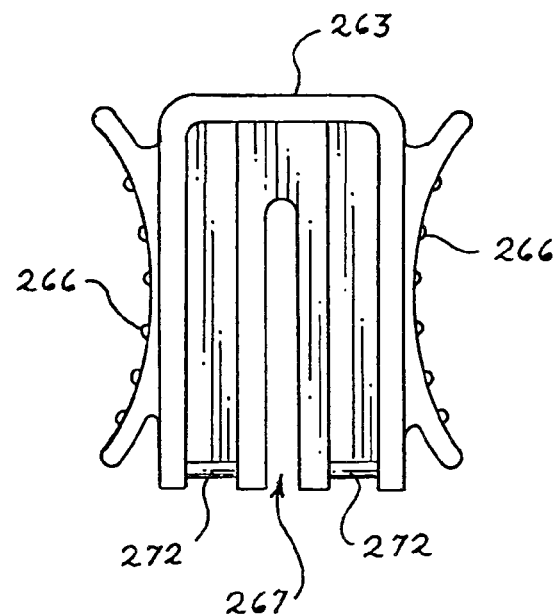
Figure 3C:
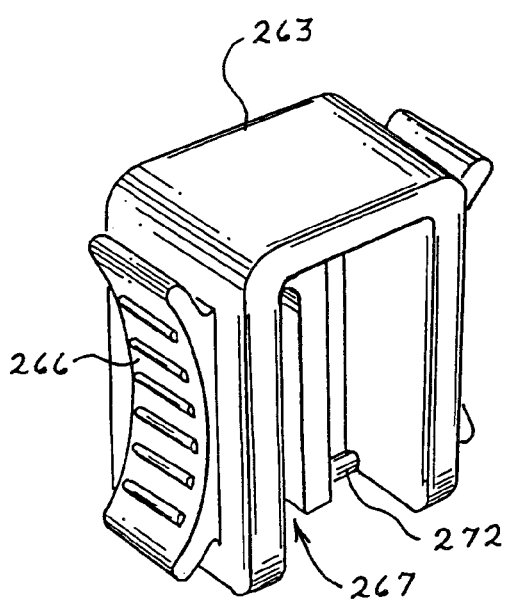
FIG. 3c is a perspective view of the handle cap of FIG. 3b.

The cap 263 is illustrated in FIGS. 1a, 3b and 3c. To secure the T-shaped fitting 141 within the cavity 260, the fitting 141 is pushed to the proximal end of the cavity and the cap 263 is pushed down and secured within the cavity 260. As shown in FIGS. 3b and 3c, the cap 263 has finger grips 266 on either side, as well as a central slot 267 and a lip portion 272. The finger grips 266 are designed to enhance friction between the user's fingers and the cap 263 to make it easier to secure and remove the cap 263 within the cavity 260. To secure the cap 263 within the cavity 260, the two lip portions 272 are aligned with the two mirror-image side slots 264 of the cavity illustrated in FIG. 3a. The cap 263 can then be pushed downwards until the lips 272 engage the center notch 273 of the side slot. The center notches 273 are merely an intermediate stopping point, and are provided so that the cap 263 is not easily removed from the cavity 260.

To secure the inner cannula 14 within the cavity 260, the cap 263 must be pushed all the way down until the lips 272 engage the bottom notches 271 of the cavity's side slots 264. Both the center notches 273 and the bottom notches 271 are slightly wider than the rest of the side slots 264. As such, these notches will hold the cap 263 in place by prohibiting the lips 272 from moving into the more narrow portions of the side slots 264 without additional force being exerted on the cap 263 by the user. Once the cap 263 is pushed down and the lips 273 are engaged in the bottom notches 271, the center slot of the cap 267 will be aligned with the slot of the first end 261.

The handle 16, the outer cannula 12, the cap 263, the inner cannula, and the extraction cannula 15 cooperate to extend the extraction device from the outer cannula 12 and retract the extraction device. The basket 18 preferably is made so that it extends about 2.7 cm plus or minus 2 mm (about 1.05 inches plus or minus about 0.08 inches). Other extensions may be used. The basket will extend to the extent that the inner cannula is moved by the surgeon applying force and translating the inner cannula inside the outer cannula 12. Because the wires necessarily are not straight, but curve to form a basket, it is necessary for a translation of about 4 cm (about 1.6 inches) on the inner cannula to extend a basket of about 2.7 cm (about 1.1 inches). The handle 16 should be designed and made so that squeezing the handle 16 causes the first end 161 to deflect the desired amount by the time the first end contacts the second end 162 and no further translation of the inner cannula or the basket is possible. In a preferred embodiment, when the basket extends about 2.7 cm (about 1.1 inches) from the end of the outer cannula 12, the width of the basket (diameter) is about 1.8 cm, plus or minus about 2 mm (about 0.71 inches plus or minus about 0.08 inches). Other configurations may be used.

The wires used to form the basket are preferably a superelastic shape-memory material, such as Nitinol, a Ni—Ti alloy. Other alloys, such as Cu—Zn—Al, or Cu—Al—Ni may also be used. Round wires are preferably used to form the basket, but triangular and flat wires may also be used. Wires having a diameter of from about 0.08 mm to about 0.15 mm (about 0.003 inches to about 0.006 inches) are preferred, because their use permits a very small diameter basket, and hence a small diameter cannula. It is also preferred that the wires and the small loops used to restrict movement of the wires be kink-free. This is achieved by using the shape-memory metals mentioned above, and heat treating them in the desired shape for a short period of time.

Shape-memory or superelastic materials are heat treated or annealed from a weak (martinsite) structure to a strong (austenite) structure. The alloys are weak and deformable in the martinsitic state, which is thus useful for forming the basket and the loops. After transformation to the strong or martensitic state, they exhibit a superelastic property so long as the material remains above a transformation temperature, at which temperature it will revert to the martensitic state. The transformation temperature is desirably a low temperature, well below the temperature of a human body, and preferably below room temperature, about 20-25° C. The transformation temperature of the wires and the basket is thus selected to be below the operating temperature of the basket, thus keeping the basket in a superelastic state. In this state, the wires advantageously return to their original, unstressed shape when deforming stresses are removed. The superelastic wire alloy also increasingly resists deformation as the stress load is increased. Thus, when a superelastic basket is collapsed and placed into the cannula, a stress load is placed on the basket. When the basket is deployed, the stresses are removed, and the basket returns to the desired shape.

The baskets are formed by shaping the wires and loops into the desired shape at room temperature or below, preferably with one or more cold mandrels, and then annealing the properly-shaped basket at the proper annealing temperature for a time sufficient for the transformation to a superelastic state. In one example, a basket is formed from 0.15 mm diameter (about 0.006 inches) Ni—Ti Nitinol wire and is annealed at 800° F. (about 427° C.) for about 10 minutes. The time and temperature for annealing will vary with the alloy selected and with the diameter (thickness) of the wire. The basket itself, not the annealing oven, must remain at the desired annealing temperature for the proper length of time for annealing to be complete. Proper annealing is very important for the wires and the loops to remain kink-free during deployment and operation of the basket. If kinks form for any reason, it may be difficult to deploy (expand) or retract the basket.

The basket is desirably formed before the annealing operation, as discussed above, including all wires and loops. It is preferred for the small loops formed in the wires to be arranged so that the loops are on the inside of the basket, rather than the outside. Having small loops on the inside of the basket is advantageous in two ways. The loops are less likely to become kinked during basket deployment and maneuvers. And the basket and extractor are less likely to cause trauma to tissue that is contacted by the basket, i.e., the basket and the extractor are then atraumatic. Of course, the loops are not likely to cause trauma even if they are outside the basket, but they are preferred on the inside.

Figure 1C:
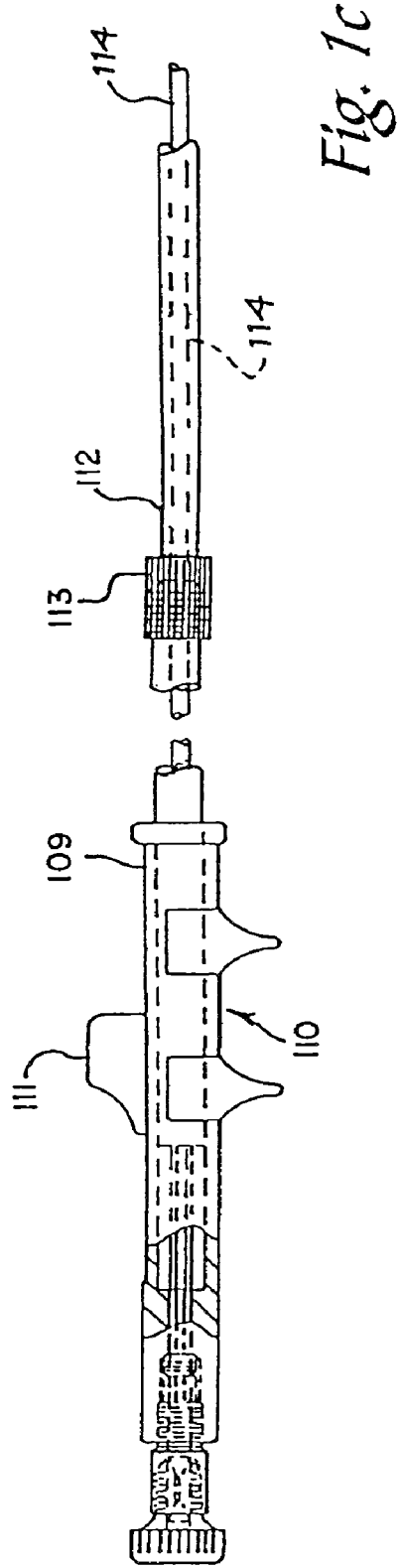
FIG. 1c is a plan view of another embodiment of a rigid extractor.
Figure 1D:
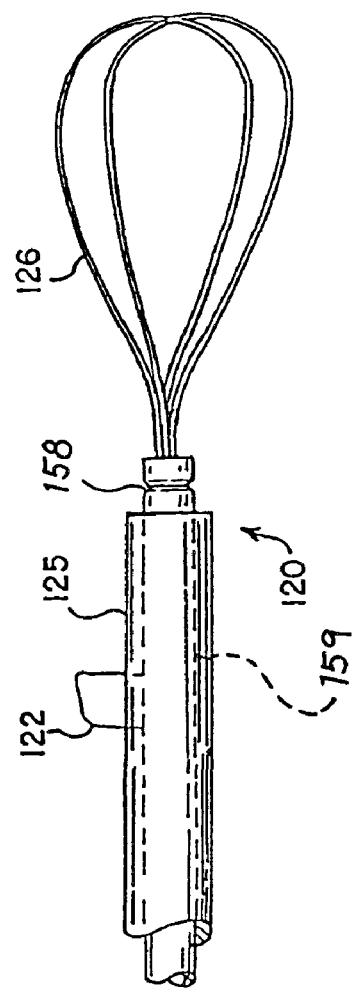
FIG. 1d is a plan view of yet another embodiment of a rigid extractor.

FIGS. 1c and 1d feature alternate embodiments of the rigid extractor. While the handle depicted in FIG. 1a is preferred, other handles and configurations may be used. FIG. 1c depicts an embodiment of a rigid extractor 110 in which the outer cannula 112 is fixed to a handle 109 with a fitting 113 while the proximal end of the movable inner cannula 114 (shown in dotted line) is attached to a control button 111. A tipless, atraumatic basket (not shown) is attached to the distal end of the inner cannula. FIG. 1d depicts an even simpler embodiment 120 of a tipless atraumatic basket 126 with a rigid outer cannula 125. In this embodiment, the basket 126 is affixed to the inner cannula 147 by a crimp joint 148. The inner cannula 147 and control button 122 are used to deploy the basket 126 from the outer cannula 125 to encircle and remove stones or calculi from a body.

Figure 5:
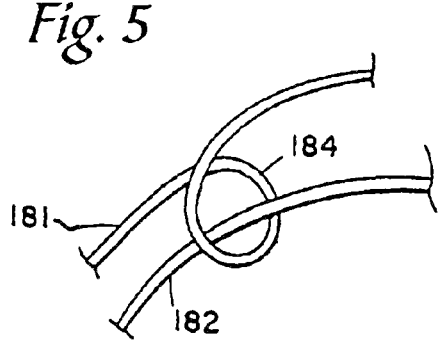
FIGS. 5-10 are embodiments of loops for the wires forming a basket for the retrieval device of FIGS. 1a and 1b.
Figure 6:
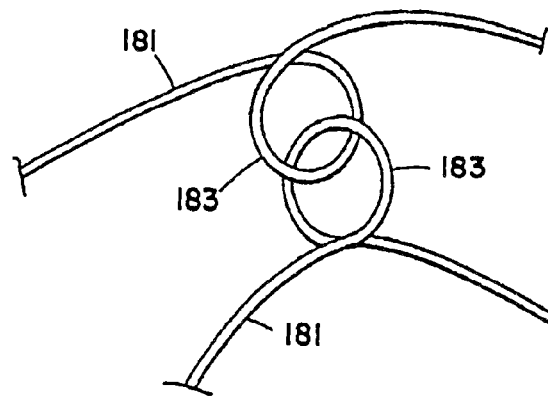

FIGS. 5-10 depict several embodiments of small loops that may be used to restrict movement of the wires, large loops, and legs that form the basket for the rigid extractor. In FIG. 5, a basket is formed from two large loops 181, 182, wherein large loop 181 is formed with an integral small loop 184 that encircles the other large loop 182. The diameter of the small loop is desirably formed as small as possible without kinking. FIG. 6 depicts a basket formed from two wires 181, each formed with a small loop 183 that encircles the other small loop. In both FIGS. 5 and 6, the small loops will coincide with the outer portion of the basket formed.

Figure 7:
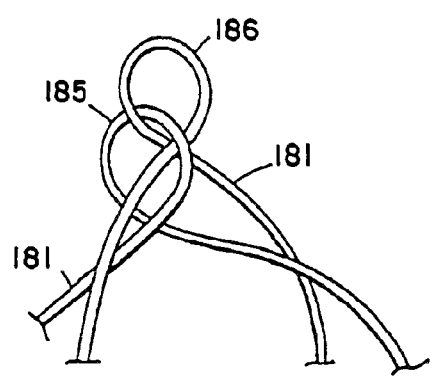
Figure 8:
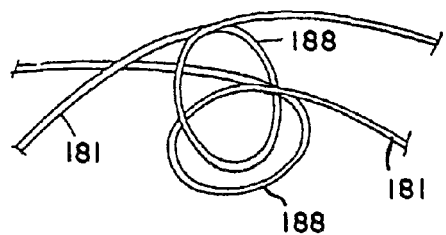

In FIG. 7, a first wire 181 is formed with a small loop 185 and a second wire 181 is formed with a small loop 186, the small loops intertwined with the wires in such a manner that the loops are external to the basket, that is, the small loops depend outwardly from at least one of the large loops. This is not a preferred embodiment, because the small loops desirably are formed inside the basket, and thus preferably depend inwardly from the large loops. Such a desirable configuration is depicted in FIG. 8. In this preferred embodiment, a first wire 181 is formed with a small loop 188 and a second wire 181 is also formed with a small loop 188. The small loops intertwine as shown, and will be contained within the basket, i.e., the small loops will depend inwardly from the large loops.

Figure 9:
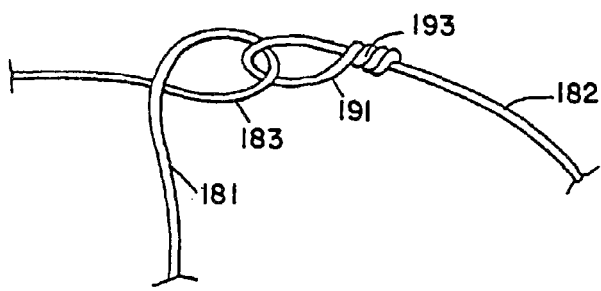
Figure 10:
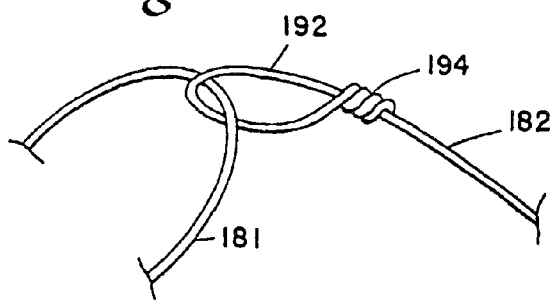

The embodiments of FIGS. 5-8 have used large-loop wires, in which a wire starts at the inner cannula with one end, forms part of a basket at its middle, and terminates at the inner cannula with the other end of the wire. Other embodiments of the basket may use a single "leg," in which a wire starts at the inner cannula at one end, and then terminates at the basket, as shown in FIGS. 9-10. In FIG. 9, a large loop of wire 181 is formed with a small loop 183, while a wire leg 182 terminates with a small loop 191, the small loops 183, 191 intertwining and acting to restrict movement of both the wire loop 181 and the leg 182. In both FIG. 9 and FIG. 10, leg 182 should be terminated back upon itself in a joint 193, 194 that has no sharp edges or burrs. This will ensure that the basket and the extractor will remain atraumatic.

The rigid extractor with tipless, atraumatic, shape-memory basket may be used with a nephroscope, as mentioned above, or it may also be used directly, with a fluoroscope to aid the surgeon in manipulating the extractor to find, encircle, and remove a kidney stone or other object within a body. The method is preferably used after lithotripsy, in which the kidney stones are reduced in size by the application of sound energy, laser energy, electro-hydraulic energy, or other outside source of energy to reduce the stones in size. In one method of using the extractor, a needle is inserted below the 12th rib of a patient. A wire guide is inserted into the region of interest, and the opening is dilated sequentially by a series of small but increasingly larger tubes. In this manner, a final tube up to 26 Fr to 30 Fr may be used. If desired, an access sheath, such as a PTFE access sheath, may be subsequently inserted and the dilation tube removed. The rigid extractor is then inserted through the access sheath. As mentioned above, nephroscopy and a nephroscope may be used instead of fluoroscopy.

As noted above, the rigid cannula is expected to find use in procedures for removing kidney stones from patients. The rigid extractor may also be used in other applications, such as the urinary, biliary, vascular or other systems. The details of the construction or composition of the various elements of the rigid extractor, the outer cannula 12, the inner cannula, and the basket, not otherwise disclosed are not believed to be important to the achievement of the advantages of the present invention, so long as the elements possess the strength or rigidity or elasticity, as described above, as needed to perform as desired. The selection of such details of construction are believed to be well within the ability of one having skill in the art, in view of the present disclosure.

Figure 11:
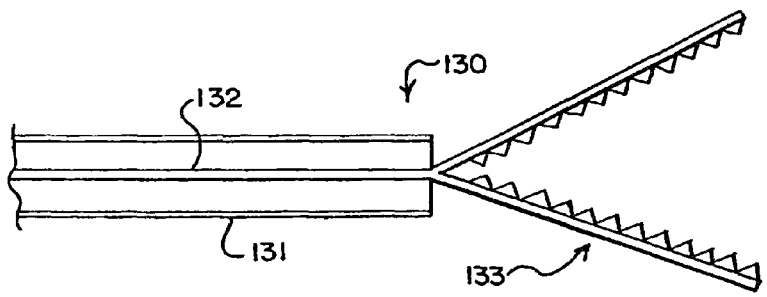
FIGS. 11 and 12 are grasper embodiments of the rigid extractor.

Other embodiments may also be made using retrieval devices other than a basket, such as a jaw-type retrieval assembly or a scissors-type retrieval assembly. A grasper assembly could also be used, and although a basket-type retrieval assembly may be preferable, a grasper that is easier to place and control by a surgeon may have its place among medical retrieval devices. A rigid cannula and controlled-force handle may be used with these other retrieval assemblies, as depicted in FIGS. 11-19. FIG. 11 depicts an extractor 130 with a jaw-type retrieval device 133 for grasping an object within a body. A user extends the jaws from the rigid outer cannula 131 and actuates the jaws using inner cannula 14, which is preferably removably secured to the extraction cannula 132 and control handle 16. Shape-memory metals may be used so that the jaws are in a relaxed state when extended from the outer cannula and in a stressed state when they are in the cannula.

Figure 12:
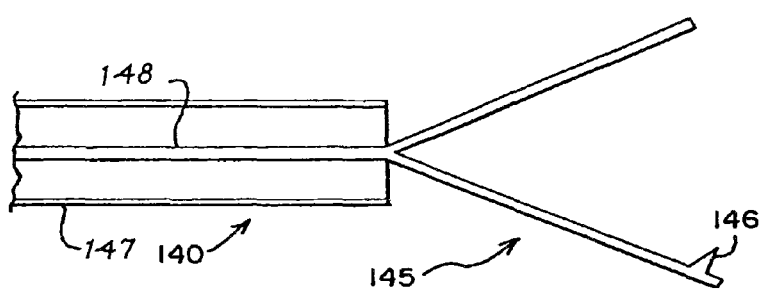

FIG. 12 depicts an embodiment of an extractor 140 with a scissors-type retrieval assembly 145 for cutting, as for a biopsy. In this embodiment, the scissors-type retrieval assembly is controlled by the inner cannula, which is preferably removably secured to the extraction cannula 148 and control handle 16. When the scissors are extended from the outer cannula 147, they separate and may be used for cutting. The scissors may be equipped with a "mouse tooth" 146 for impaling an object within a body. Shape-memory metals may be used so that the scissors are in a relaxed state when extended from the outer cannula 147 and in a stressed state when they are in the cannula. The basket described above, and the jaws and the scissors described here, may be considered as retrieval assemblies or devices at the distal end of the inner cannula. The rigid outer cannula is used to maneuver the extractor near the object to be removed, so that the retrieval assembly, whether basket, jaws, scissors, or grasper or other retrieval device, may be used to remove the object. Preferably, each retrieval assembly or device is connected to an extraction cannula removably secured to the inner cannula 14 with mating threaded portions 143, 153, as depicted in FIG. 2a. Alternatively the extraction cannula may be secured to the inner cannula 14 with a snap fit connection 155, 157 as shown in FIG. 2c, or any other means known in the art.

Figure 13:
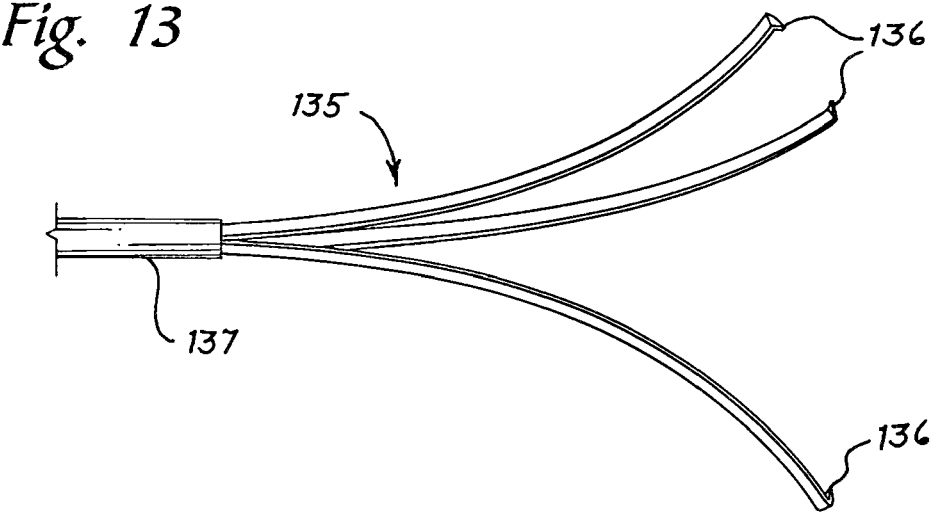
FIG. 13 is a three-prong grasper embodiment of the rigid extractor.

FIG. 13 depicts an embodiment of an extractor 135 of the three-prong variety. The three-prong grasper 135 may be equipped with three inward-facing "mouse tooth" projections 136 for grasping calculi. The three-pronged grasper 135 may be secured to an extraction cannula, which in turn is removably secured to the inner cannula 14. A user extends the three-pronged grasper 135 from the rigid outer cannula 137 and actuates the grasper 135 using the inner cannula 14 and the control handle 16. Shape-memory metals may be used so that the three-pronged grasper is in a relaxed state when extended from the outer cannula 137 and in a stressed state when they are in the cannula 137.

Figure 14:
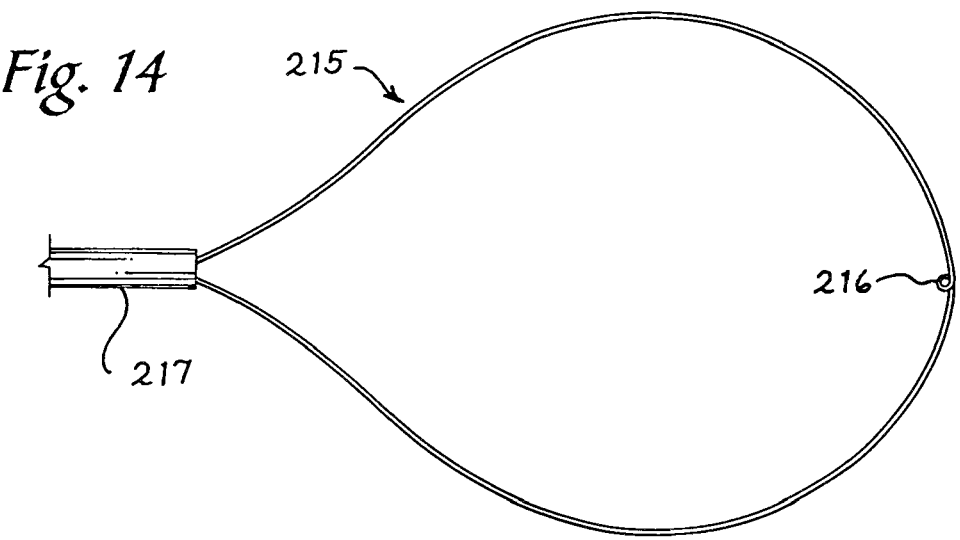
FIG. 14 is a retrieval loop embodiment of the rigid extractor.

FIG. 14 depicts an embodiment of an extractor 215 of the single-loop variety. The single-loop extractor 215 may be equipped with a single knot or loop 216 at its distal end. The single-loop extractor 215 may be secured to an extraction cannula, which in turn is removably secured to the inner cannula 14. A user extends the single-loop extractor 215 from the rigid outer cannula 217 and actuates the extractor 215 using the inner cannula 14 and the control handle 16. Shape-memory metals may be used so that the single-loop extractor is in a relaxed state when extended from the outer cannula 217 and in a stressed state when inside the cannula 217.

Figure 15:
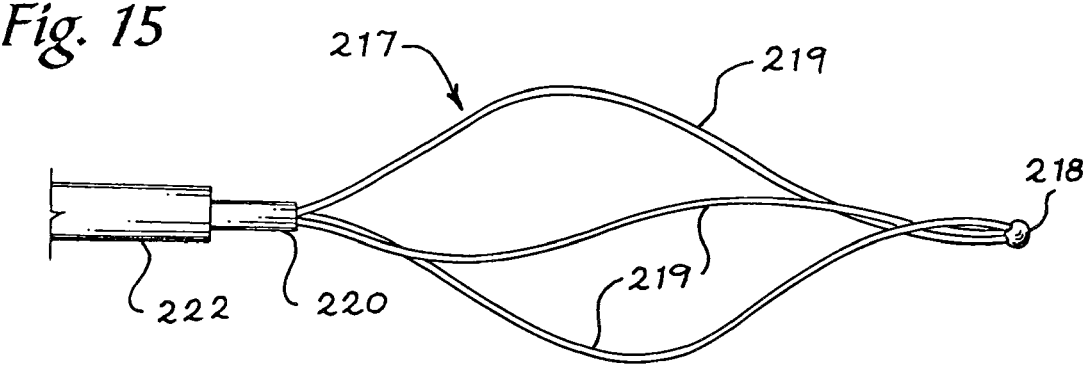
FIG. 15 is a helical three-wire basket embodiment of the rigid extractor.

FIG. 15 depicts an embodiment of a helical extractor 217. The helical extractor 217 may be equipped with a solder joint 218 at its tip. Alternatively, a braze joint or weld joint can be used to join the wires 219 to form a distal end of the helical basket 217. In this embodiment, a solder joint joins the three wires 219, which are secured to the extraction cannula 220. Again, the extraction cannula 220 is preferably removably secured to the inner cannula 14. The three wires 219 are made from a shape-memory metal so that the three wires 219 form the helical extractor or basket formation, shown in FIG. 15, when in a relaxed state extended from the outer cannula 222. The helical extractor 217 is in a stressed state when it is inside the outer cannula 222. A user extends the helical extractor 217 from the rigid outer cannula 217 and actuates the extractor 217 using the inner cannula 14 and the control handle 16.

Figure 16:
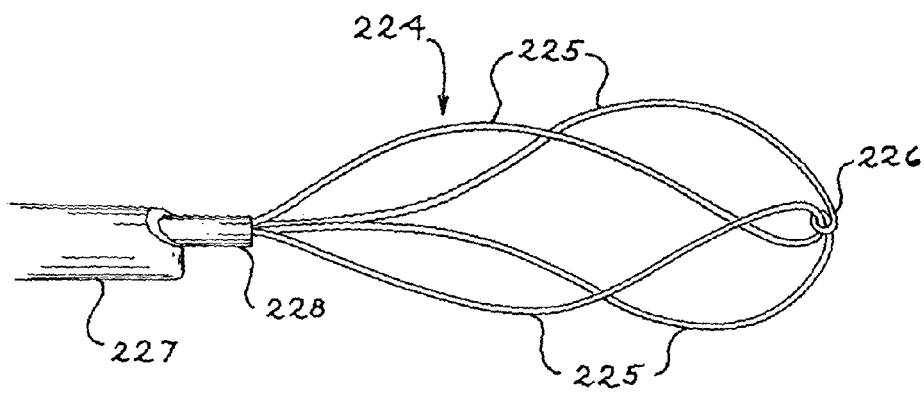
FIG. 16 is a helical tipless basket embodiment of the rigid extractor.

FIG. 16 depicts an embodiment of a helical tipless extractor 224. The helical tipless extractor 224 may be equipped with a knot or loop 218 at its distal end. In this embodiment, four wire segments 225 form the helical tipless basket, and the four wire segments 225 are secured to the extraction cannula 228. Again, the extraction cannula 228 is preferably removably secured to the inner cannula 14. The four wire segments 225 are made from a shape-memory metal so that the wire segments 225 form the helical extractor or basket formation, shown in FIG. 16, when in a relaxed state extended from the outer cannula 227. The helical tipless extractor 224 is in a stressed state when it is inside the outer cannula 227. A user extends the helical tipless extractor 224 from the rigid outer cannula 227 and actuates the extractor 224 using the inner cannula 14 and the control handle 16.

Figure 17:
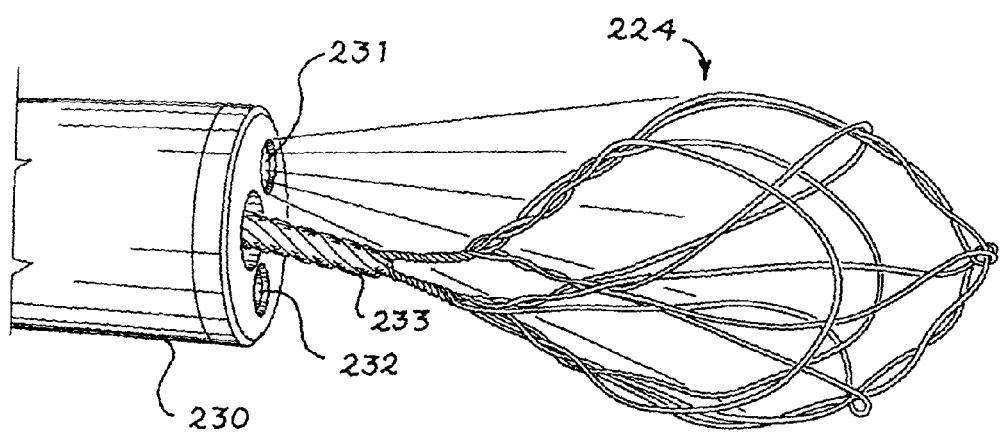
FIG. 17 is a multi-wire basket embodiment of the rigid extractor.
Figure 18:
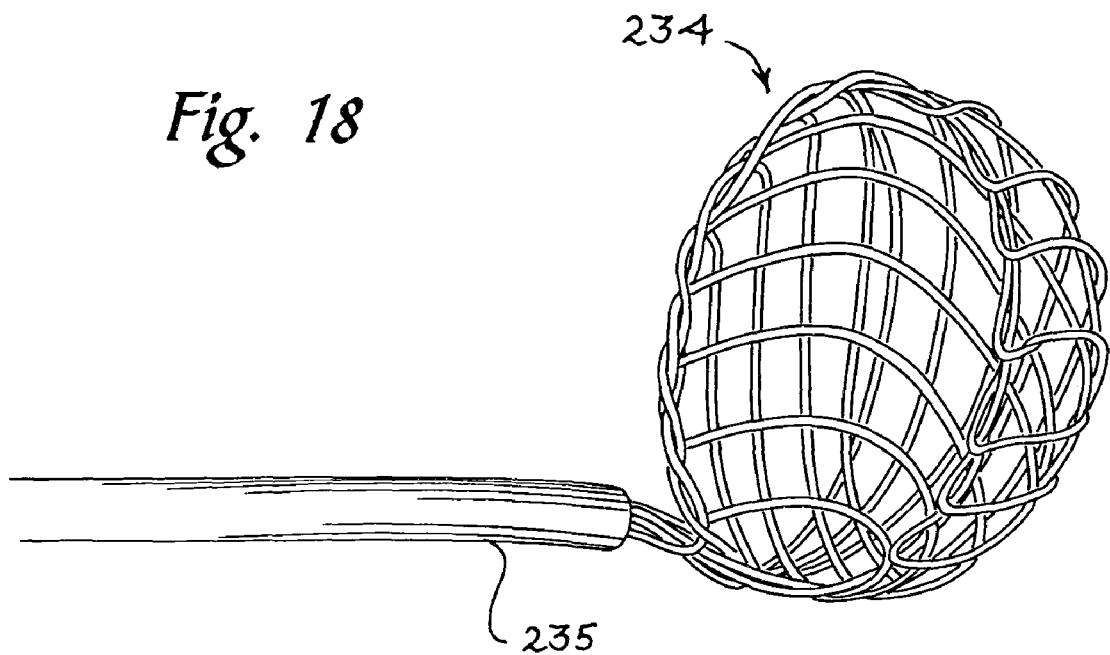
FIG. 18 is another multi-wire basket embodiment of the rigid extractor.

FIGS. 17 and 18 depict embodiments of multiple-wire baskets. FIG. 17 depicts a multiple-wire basket 229 which is designed to improve stone-free rates. The multi-wire geometry provides a tight weave designed to capture routine stones as well as small fragments left behind following a procedure such as an intracorporeal lithotripsy. In addition, this embodiment may be used with an outer cannula 230 of a larger diameter and including additional openings 231, 232 for providing a surgeon with light, or additional surgical tools. The multiple-wire basket 229 geometry may be created as a twelve or sixteen wire basket. In this embodiment, the multiple wire segments which form the basket 229 are secured to the extraction cannula 233. Again, the extraction cannula 233 is preferably removably secured to the inner cannula 14. The wire segments which create the basket geometry 229 are made from a shape-memory metal so that the wire segments form the basket formation, shown in FIG. 17, when in a relaxed state while extended from the outer cannula 230. The basket 229 is in a stressed state when it is inside the outer cannula 230. A user extends the basket 229 from the rigid outer cannula 230 and actuates the basket 229 using the inner cannula 14 and the control handle 161.

FIG. 18 depicts a multiple-wire basket embodiment 234 with an umbrella design. As with the multiple-wire basket of FIG. 17, the umbrella basket 234 is made from wire segments of a shape-memory metal so that the wire segments form the umbrella basket when in a relaxed state while extended from the outer cannula 235. The basket 234 is in a stressed state when inside the outer cannula 235. As before, a user extends the basket 234 from the rigid outer cannula 235 and actuates the basket 234 using the inner cannula 14 and the control handle 161. This embodiment is designed to minimize stone migration during intracorporeal lithotripsy by providing an exceptionally tight weave. In operation, the umbrella basket 234 traps stone fragments in the weave, and the surgeon can then remove the basket 234 and outer cannula 235 along with the fragments.

Figure 19:
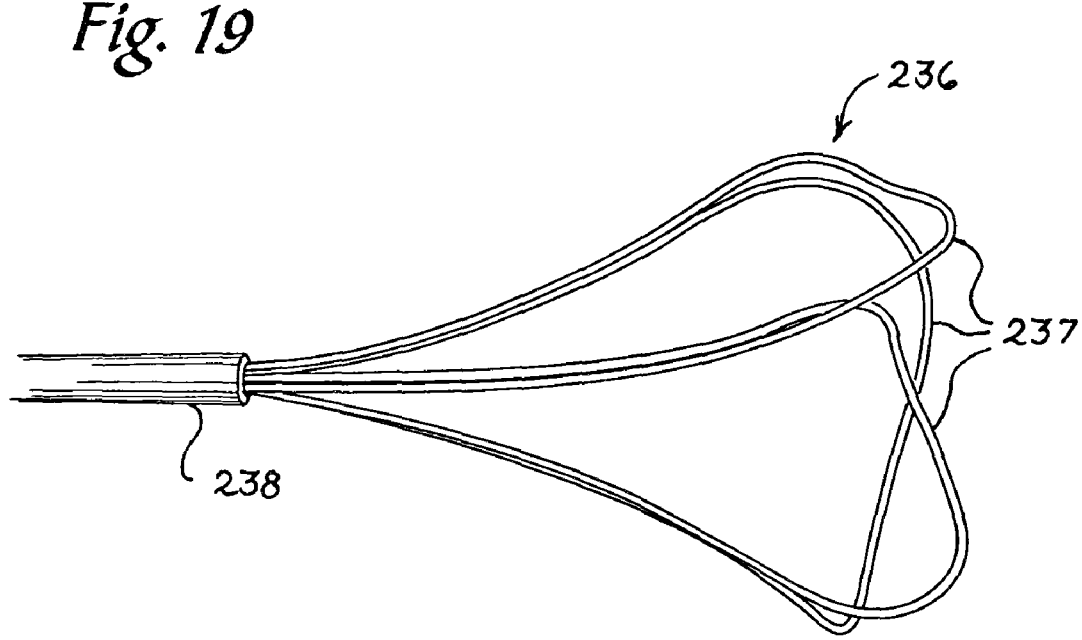
FIG. 19 is a three-loop grasper embodiment of the rigid extractor.

FIG. 19 depicts a six wire segment, three loop extractor 236. The three-loop grasper 236 may be used to engage, reposition, release, or extract stones or calculi in the kidney or the ureter. The three-loop grasper 236 may be secured to an extraction cannula, which in turn is removably secured to the inner cannula 14. A user extends the three-loop grasper 236 from the rigid outer cannula 238 and actuates the grasper 236 using the inner cannula 14 and the control handle 161. Shape-memory metals may be used so that the three-loop grasper is in a relaxed state when extended from the outer cannula 238 and in a stressed state when they are in the cannula 238.

It was noted above that the thickness of the handle (A in FIGS. 1a and 1b) determines the force that the surgeon uses to extend the basket from the sheath. If the handle 16, the inner cannula 14, the outer cannula 12, and the basket 18 are relatively free of friction, then the potential energy stored in the "squeezed" handle 16 is available for grasping a stone or other calculus. This force used to squeeze the handle 16 is stored as potential energy in the deformation of the handle 16, much as energy is stored in a compressed spring. That energy or force is applied to the stone or calculus when the surgeon releases the handle 16 and the potential energy is used to trap or "squeeze" the stone or calculus, or to operate another retrieval assembly at the distal end of the inner cannula 14. The force desired is typically that force which is sufficient to trap and hold, but not sufficient to crush or cut, the stone or calculus.

Figure 25:
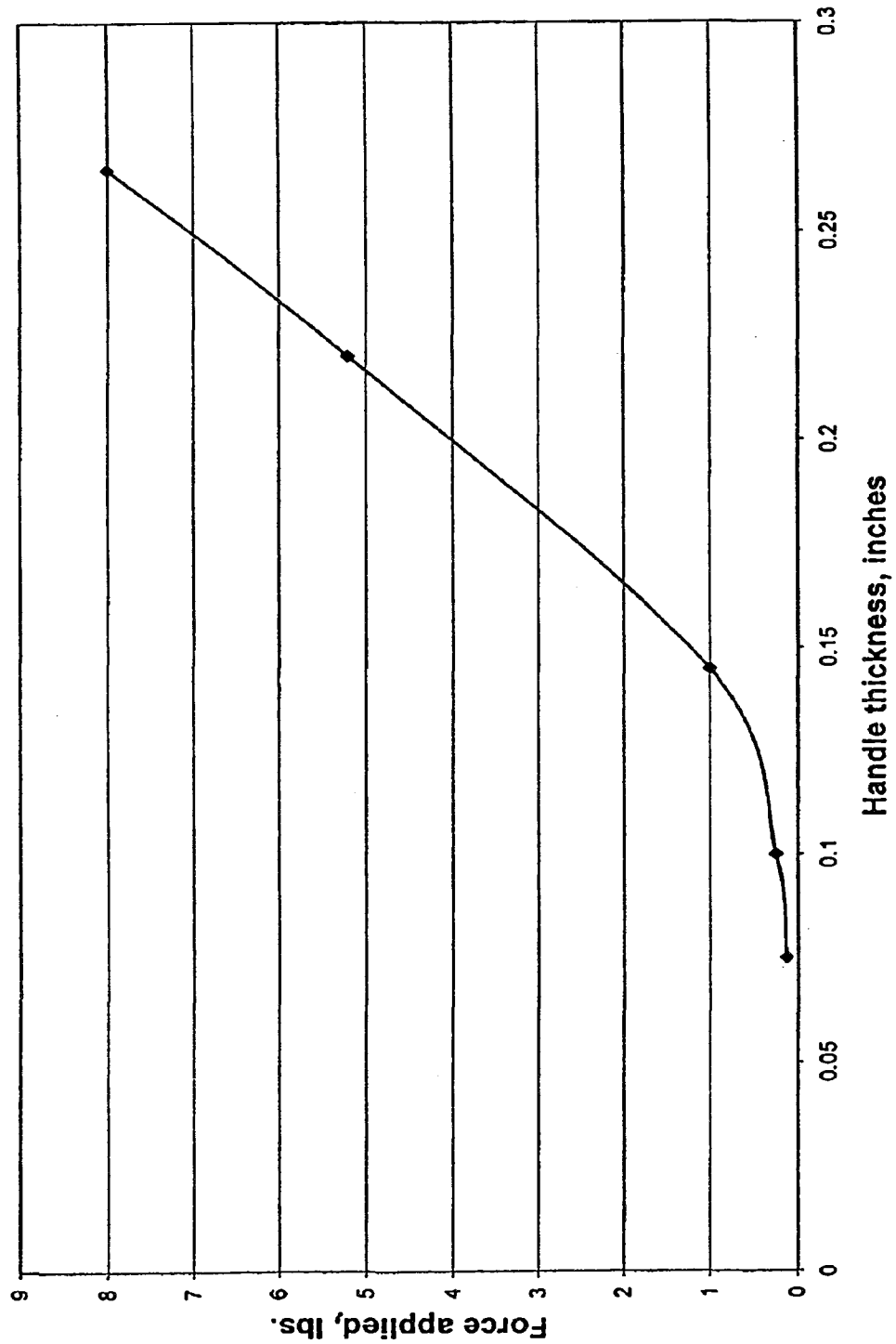
FIG. 25 is a graph of actuation force as a function of handle thickness.

A series of experiments was conducted with a rigid extractor similar to the embodiment of FIGS. 1a and 1b to determine the force available at the basket with a series of plastic handles similar to those in FIGS. 1a and 1b. The material used was Nylon 6, and the thickness of the handle 16 was varied from about 0.075 inches to about 0.28 inches. The basket was hooked to a mechanical load cell to measure the force, and the result of the experiments is shown in FIG. 25. The data suggest that the force correlates almost linearly with the handle 16 thickness, particularly if the handle 16 thickness is from about 0.15 to about 0.27 inches thick. When the thickness is less than 0.15 inches, the force drops below one or two pounds, and the effects of even small amounts of friction may govern. The force is less predictable in that range.

If the handle 16 is more than about 0.25 to 0.27 inches thick, it may require a force in excess of eight or ten pounds to extend the basket, making the handle 16 and the extractor difficult to operate. It is also clear, that besides varying the handle 16 thickness, the material may be varied, with materials of a lower flexural modulus of elasticity requiring less force while material having a higher flexural modulus will require more force. The shape of the handle 16 cross-section may also be varied, such as by adding ribs or other reinforcing members for a greater force, or by making cuts for a lesser force. Thus, the extractor provides a way to control the force used to extend the basket, and thus also control the force applied to the stone or calculus to be removed. In embodiments using a scissors or jaw-type or grasper-type assembly, the design and selection of the handle 16 allows a user to tailor the cutting or grasping force applied to the object to be removed from a body.

Figure 26:
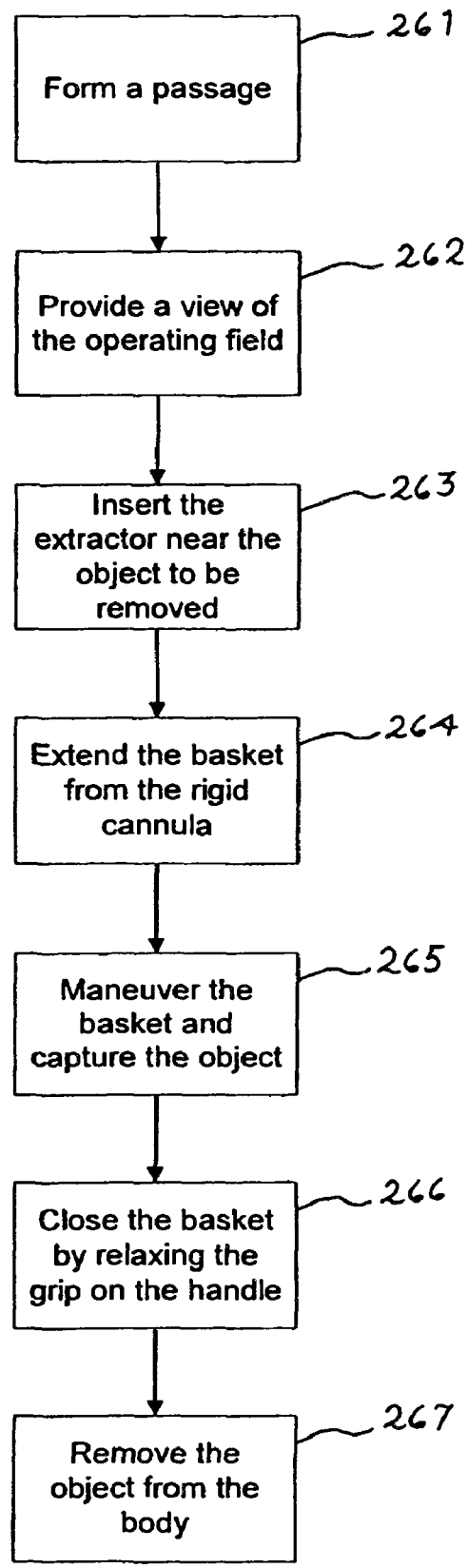
FIG. 26 is a flowchart for a method of using the rigid extractor.

FIG. 26 depicts a method used to remove stones or calculi from a body using the rigid extractor with a tipless, atraumatic basket and a rigid outer cannula. The method comprises a step 261 of forming a passage in order to insert the extractor. The next step 262 is to provide a view of the operating field for the surgeon. As discussed above, the view is preferably provided by a fluoroscope or a nephroscope. The physician then inserts the extractor 263 near the object to be removed, and then extends the basket from the rigid cannula 264. Because the cannula is rigid, it may be moved as desired, even deflecting a nephroscope if one is being used. After the basket is extended, it is necessary to maneuver the basket by using the handle 16 to capture the object 265. The basket is closed by relaxing the grip on the handle 166. Then the object is removed from the body 267.

The embodiments described above are only a few of the ways the invention may be practiced. For instance, the descriptions above have used a fixed outer cannula and a handle with a movable inner cannula attached to the basket, to move the basket forward and out of the outer cannula for deployment. Other variations may be used in which a handle moves the outer cannula backward, with a fixed inner cannula deploying the basket as the outer cannula moves rearward. The surgeon then uses the basket to capture a stone. Such variations may be used in conjunction with a plastic sheath inserted between the outer cannula and the patient. Alternatively, a plastic sheath may also be used with the embodiments of FIGS. 1a and 1b.

Figure 20:
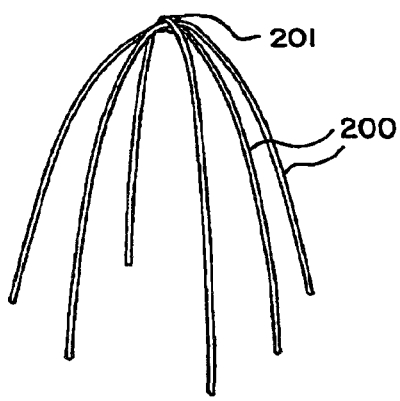
FIGS. 20-24 are alternate embodiments of a basket for the extractor.
Figure 21:
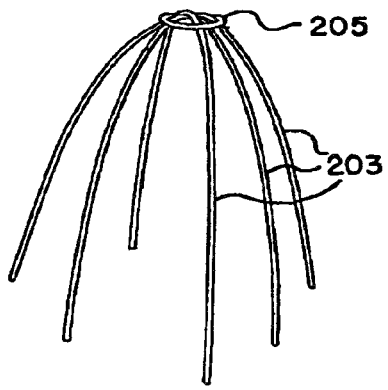

In other embodiments, the basket used for retrieval need not be limited to the tipless basket formed by looping the wires with small loops, as described above. FIGS. 20-24 depict alternate embodiments of baskets useful with the rigid cannula. In FIG. 20 for instance, the wires 200 may be secured by a knot or knots 201 in the wires themselves. In FIG. 21, a separate wire or filament 205 may be used to secure the wires 203 to form a distal end of the basket. Wire, such as Nitinol wire or other medically acceptable wire, such as stainless steel, may be used. Filaments, such as those made from suture material, or other medically-acceptable material, may also be used.

Figure 22:
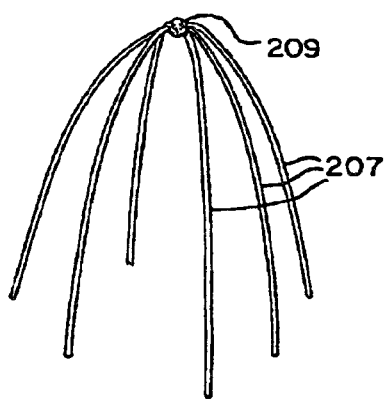
Figure 23:
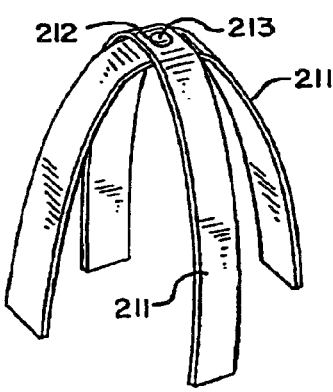
Figure 24:
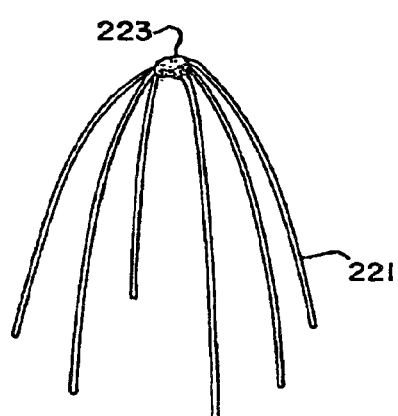

Other techniques may also be used, as shown in FIG. 22, to join wires 207 by using solder joints 209, braze joints, or weld joints, thus joining the wires to form a distal end of the basket. As shown in FIG. 23, it is even possible to drill holes 212 and use a rivet 213 to join the distal ends of wires 211, to form a distal end of the basket. The rivet embodiment is better accomplished with flat wire than with round wire. Other embodiments, as shown in FIG. 24, may use a small elastomeric or plastic fastener or ball 223 to join the distal ends of wires 221 to form a distal end of a basket useful in the rigid extractor embodiments of the present invention.

Accordingly, it is the intention of the applicants to protect all variations and modifications within the valid scope of the present invention. It is intended that the invention be defined by the following claims, including all equivalents. Since the foregoing detailed description has described only a few of the many alternative forms this invention can take, it is intended that only the following claims, including all equivalents, be regarded as a definition of this invention.

What is claimed is:

1. An extractor for removing an object from a location within a body, the extractor comprising:
   an inner cannula with a proximal end comprising a restriction member and a distal end, the distal end having a removable extraction device;
   an outer cannula;
   a handle having a first end and a second end, the first end fixedly attached to the outer cannula and the second end removably receiving the restriction member,
   the second end comprising a hollow portion defining a central slot configured to slidably receive the restriction member, two side slots are defined blindly along opposite walls of the second end; and
   further comprising a cap with two lip portions that are configured to be slidably received within the two side slots when the cap is disposed upon the second end.

2. The extractor of claim 1, wherein the second end of the handle includes an open-top cavity in communication with the slot, the slot opening towards the first end of the handle.

3. The extractor of claim 2, wherein the central slot is sized such that the inner cannula is capable of free movement along the length of the central slot.

4. The extractor of claim 1, wherein the inner cannula includes a threaded portion at its distal end, and the removable extraction device has a mating threaded portion at its proximal end.

5. The extractor of claim 4, wherein the threaded portion of the extraction device is disposed about 5 mm to about 10 mm from the most distal portion of the extraction device.

6. The extractor of claim 1 wherein the inner cannula includes a snap-fit portion at its distal end, and the removable extraction device has a mating snap-fit portion at its proximal end.

7. The extractor of claim 1 wherein the inner cannula is a solid rod.

8. The extractor of claim 1, wherein the removable extraction device includes a Nitinol alloy.

9. The extractor of claim 1 wherein the extraction device is chosen from a group consisting of a three-prong grasper, a two-prong grasper, and a multiple-wire basket.

10. The extractor of claim 1 wherein the extraction device includes at least one superelastic wire loop, and the at least one superelastic loop forms a reversibly collapsible, tipless, atraumatic basket.

11. The extractor of claim 1, wherein the handle is made from nylon and is from about 0.15 to about 0.30 inches thick and from about 0.125 inches to about 0.75 inches wide.

12. The extractor of claim 1, wherein the handle is made from plastic and is from about 0.15 to about 0.30 inches thick.

13. The extractor of claim 1, wherein the handle is made from metal and is from about 0.15 to about 0.30 inches thick.

14. The extractor of claim 1, wherein each of the two side slots have an arcuate central notch defined therein.

15. The extractor of claim 1, wherein each of the two side slots have arcuate bottom notches configured to receive the lip portions therein when the cap is disposed upon the second end.

16. The extractor of claim 1, wherein the cap has slot disposed in registry with the central a slot when the cap is disposed upon the second end.

* * * * *

UNITED STATES PATENT AND TRADEMARK OFFICE
CERTIFICATE OF CORRECTION

| | | |
|---|---|---|
| PATENT NO. | : 8,043,303 B2 | Page 1 of 1 |
| APPLICATION NO. | : 12/177446 | |
| DATED | : October 25, 2011 | |
| INVENTOR(S) | : Hassan Razvi et al. | |

It is certified that error appears in the above-identified patent and that said Letters Patent is hereby corrected as shown below:

In the Claims

In column 14, claim 16, line 52, after "wherein the cap has" insert --a--.

Signed and Sealed this
Third Day of January, 2012

David J. Kappos
*Director of the United States Patent and Trademark Office*